United States Patent [19]

Horino et al.

[11] Patent Number: 5,744,126
[45] Date of Patent: Apr. 28, 1998

[54] COSMETICS CONTAINING SILICONE SURFACE-MODIFIED PARTICLES OF TITANIUM OXIDE AND ZINC OXIDE

[75] Inventors: Masaakira Horino, Sagamihara; Yukio Hasegawa, Kasukabe, both of Japan

[73] Assignee: Miyoshi Kasei, Inc., Saitama, Japan

[21] Appl. No.: 656,369

[22] Filed: May 31, 1996

[30] Foreign Application Priority Data

Jun. 2, 1995 [JP] Japan ................... 7-158814
May 1, 1996 [JP] Japan ................... 8-134280

[51] Int. Cl.$^6$ ............... A61K 7/42; A61K 7/44; C09D 1/00; C09C 1/02
[52] U.S. Cl. ............ 424/59; 424/60; 106/286.4; 106/286.6; 106/465
[58] Field of Search ............... 106/490, 287.11, 106/287.12, 465, 493; 424/59, 60, 63, 64

[56] References Cited

U.S. PATENT DOCUMENTS

| | | | |
|---|---|---|---|
| 5,458,681 | 10/1995 | Hasegawa et al. | 106/490 |
| 5,543,136 | 8/1996 | Aldous | 424/59 |
| 5,573,753 | 11/1996 | Tapley | 424/59 |

FOREIGN PATENT DOCUMENTS

| | | |
|---|---|---|
| 47-42502 | 10/1972 | Japan. |
| 58-62106 | 4/1983 | Japan. |
| 61-229809 | 10/1986 | Japan. |
| 62-228006 | 10/1987 | Japan. |
| 2-194065 | 7/1990 | Japan. |
| 2-196028 | 8/1990 | Japan. |
| 2-196029 | 8/1990 | Japan. |
| 3-199121 | 8/1991 | Japan. |
| 3-279323 | 12/1991 | Japan. |
| 6-59397 | 8/1994 | Japan. |
| 7-23294 | 3/1995 | Japan. |

*Primary Examiner*—Laurie Scheiner
*Assistant Examiner*—Jeffrey S. Parkin
*Attorney, Agent, or Firm*—Armstrong, Westerman, Hattori, McLeland & Naughton

[57] ABSTRACT

Cosmetics having good dispersibility, high sustained ultraviolet light ray shielding, suppressed photochemical reactivity and catalytic activity of the ultraviolet ray shielding material and high stability. A milky lotion containing fine particles of zinc oxide surface-modified with 5% dimethyl polysiloxane (mean particle size, 1.6µ) and titanium oxide surface-modified with 5% dimethyl polysiloxane (mean particle size, 1.2µ).

11 Claims, No Drawings

5,744,126

1

COSMETICS CONTAINING SILICONE SURFACE-MODIFIED PARTICLES OF TITANIUM OXIDE AND ZINC OXIDE

FIELD OF THE INVENTION

This invention relates to cosmetics. More particularly, it relates to cosmetics exhibiting good dispersibility, high ultraviolet rays shielding effects and high stability against changes with lapse of time and which can suppress photochemical reactivity and catalytic activity of the ultraviolet rays shielding material.

BACKGROUND OF THE INVENTION

Related Art

The ultraviolet rays are known to produce various ill effects on the skin. The ultraviolet rays are classified into a long wavelength ultraviolet rays having a wavelength of 400 to 320 nm (UV-A rays), a mid wavelength ultraviolet rays having a wavelength of 320 to 290 nm (UV-B rays) and ultraviolet rays having a wavelength not longer than 290 nm (UV-C rays). The UV-C rays are absorbed by the ozone layer without reaching the ground surface. If the UV-B rays reaching the ground are absorbed by the skin in a quantity in excess of a pre-determined quantity, erythema or blisters are formed, thus promoting melamine formation. On the other hand, the UV-A rays are substantially weaker than the UV-B rays in erythema inducing properties, such that the skin is pigmented(darkened) without substantially inducing erythema. In addition, the UV-A rays exhibit high permeability to skin to promote cross-linking of collagen, which is the skin protein, thus lowering flexibility of collagen and water retention properties and inducing wrinkles. Also the UV-A rays can cause stains and freckles thus inducing ageing of the skin. The UV-A rays are also known to increase lipid peroxides in the skin structure thus occasionally causing skin cancer.

For possibly protecting the skin from these hindrance by the ultraviolet rays, cosmetics containing a variety of ultraviolet ray absorbing agents have been developed and marketed. Among these cosmetics, there are synthetic ultraviolet ray absorbing agents, such as benzophenones, amino benzoates, cinnamic acid esters, benzotriazoles, salicylic acids or dibenzoyl methane, and fine particles of inorganic pigments such as titanium oxide, zinc oxide or iron oxide.

DISCUSSION OF RELATED ART

However, there are grave problems in the art, according to the keen analyses by the present inventors as discussed hereinbelow.

The synthetic ultraviolet ray absorbing agents exhibit lower dispersibility or solubility in oil ingredients of cosmetics with increasing amount of addition such that sufficient performance proper to the ultraviolet ray absorbing agents cannot be displayed. Most effective absorbers against the UV-A rays are benzotriazoles and dibenzoylmethane. However, these are solid and poor in solubility in cosmetic oil ingredients at ambient temperature. In addition, with an oil gel or an emulsified product, crystals of pale yellow color tend to be precipitated with lapse of time in the presence of small quantities of metal ions or soft particulate lumps of yellow to orange color due to complex formation tend to be precipitated and distributed to detract the commercial value through the appearance of the finished product.

Thus, for shielding the ultraviolet rays over a wide range, ultraviolet ray scattering agents are used. As the ultraviolet

2 ray scattering agents, ultra-fine particles of inorganic (metal) oxides, such as titanium oxide, zinc oxide, zirconium oxide, cerium oxide or iron oxide, are used, usually as ingredients of sunscreen type cosmetics. These ultraviolet ray scattering inorganic agents, used for their high safety for the skin and capacity of shielding the ultraviolet rays over a wide range, are not entirely satisfactory since they suffer from defects as indicated by the following Publications.

Thus, in JP Patent Kokoku publication JP-B-47-42502 (1972), there is disclosed an anti-sunburn cosmetic containing titanium oxide with a mean particle size of 30 to 40 mμ; shields the UV-B rays. However, titanium oxide is essentially a substance shielding the UV-B rays but is not capable of shielding the UV-A rays unless it is added at a high ratio. Due to such addition at the high ratio of titanium oxide, the resulting cosmetics become visibly white when applied to the skin and aesthetically unsatisfactory, with additional drawbacks that the cosmetics have undesirably poor dispersibility in its formulations, feeling and stability.

There is proposed in JP Patent Kokai Publication JP-A-58-62106 (1983) a cosmetic containing hydrophobilized ultra-fine particles of titanium oxide, with a particle size of 10 to 30 mμ, capable of shielding the UV-B rays. Similarly it is disclosed in the JP Patent Kokoku publication JP-B-47-42502 (1972) to use titanium dioxide. However, the ultra-fine particles of titanium oxide cannot shield the UV-A rays unless it is added at a high ratio. Due to such addition at the higher ratio of titanium oxide, the resulting cosmetics become whitening and providing coarse feel on application thus undesirably lowering extendibility or adhesion to the skin, and thus unpreferred.

There is proposed in JP Patent Kokai Publication JP-A61-229809 (1986) a cosmetic containing amorphous titanium oxide capable of shielding the UV-B rays. However, the amorphous titanium oxide cannot shield the UV-A rays unless it is added at higher ratio. Due to such addition at the higher ratio of amorphous titanium oxide, the resulting cosmetics become low in sun protection factor (SPF) due to the reflocculation or re-agglomeration of titanium oxide particulates thus providing unpreferable whitening and undesirably lowering extendibility and adhesion to the skin.

There is proposed in JP Patent Kokai Publication JP-A7-23294 (1995) a cosmetic containing ultra-fine particles of zinc oxide. The ultraviolet protection factor of the zinc oxide particles is as low as one-third to one-fourth that of the ultra-fine particles of titanium oxide, so that the zinc oxide particles need to be incorporated at higher ratio thus undesirably lowering extendibility and adhesion to the skin. In addition, oil ingredients of the cosmetics are undesirably degenerated due to strong surface activity of the ultra-fine particles of zinc oxide, thus still counted as unsatisfied.

There is proposed in JP Patent Kokai Publication JP-A-3-279323 (1991) an anti-sunburn composition containing ultra-fine particles of zinc oxide and ultra-fine particles of titanium oxide, however, high SPF values cannot be achieved unless the composition contains high ratio (at least 13 wt %). Due to addition of the high proportion of $TiO_2$ and ZnO in composition, the opacity becomes higher and whitening on skin occurs. In addition, due to re-aggregation of the particles, the SPF value is lowered, while the oil ingredients in the cosmetics become denatured and the feeling is undesirably lowered.

With such anti-sunburn composition, high SPF values may possibly be achieved directly after production of the composition. However, the ultra-fine particles of zinc oxide and the ultra-fine particles of titanium oxide in the composition exhibit surface activity so that aggregation with lapse of time (aggregation of one kind or both of the ultra-fine particles of zinc oxide and the ultra-fine particles of titanium oxide) as well as denaturing and deterioration of the oil agent contained in the cosmetics are unavoidably produced.

SUMMARY OF THE INVENTION

Thus there has been a demand for such a cosmetic which exhibits sustained high dispersibility and high ultraviolet ray protection effects and high stability, and which can suppress photochemical reactivity or catalytic activity of the ultraviolet ray scattering materials.

Therefore it is an object of the present invention to provide a cosmetic which meets said demand.

It is another object of the present invention to provide a process for producing such cosmetics.

Other objects will become apparent throughout the entire disclosure.

In view of the above-depicted status of the art, the present inventors have conducted perseverant researches, and found that, by employing surface processed products, obtained on surface-modifying and chemically bonding fine particles of titanium oxide and zinc oxide with silicone oil agents, such as dimethyl polysiloxane or methyl hydrogen polysiloxane, in a specified proportion, cosmetics having good dispersibility, suppressed photochemical reactivity and catalytic activity and high stability with lapse of time may be produced through synergistic effect thereof. This finding has led to completion of the present invention.

Namely, the present invention provides a cosmetic comprising a composition composed of a specified proportion of fine particles of titanium oxide and fine particles of zinc oxide. Specifically, the present invention provides according to a first aspect:

(i) a cosmetic comprising fine particles of titanium oxide surface-modified with silicone and fine particles of zinc oxide surface-modified with silicone.

The ratio of the fine particles of titanium oxide treated with silicone to the fine particles of zinc oxide treated with silicone is 9.8:0.2 to 5:5, preferably 9:1 to 6:4 and more preferably 8:2 to 6.8:3.2.

The mean particle size of secondary flocculation of fine particles of titanium oxide is 0.5 to 3.0 μm while the mean particle size of secondary flocculation of fine particles of zinc oxide is 0.2 to 3.5 μm.

The total weight of the fine particles of titanium oxide and the fine particles of zinc oxide is 0.5 to 12.5 wt % and preferably 1.0 to 10 wt % based on the total weight of the cosmetic.

(ii) The present invention also provides, according to a second aspect, a cosmetic comprising fine particles of titanium oxide surface-modified with silicone and fine particles of zinc oxide surface-modified with silicone. The silicone-treated fine particles of titanium oxide are obtained by pulverizing or deagglomerating titanium oxide by a jet stream and by simultaneously adsorbing and bonding silicone and the silicone-treated fine particles of zinc oxide are obtained by pulverizing or deagglomerating titanium oxide by a jet stream and by simultaneously adsorbing and bonding silicone.

The ratio by weight of the silicone-treated fine particles of titanium oxide and the silicone-treated fine particles of zinc oxide is 9.8:0.2 to 5:5, preferably 9:1 to 6:4 and more preferably 8:2 to 6.8:3.2.

The total amount of the silicone-treated fine particles of titanium oxide and the silicone-treated fine particles of zinc oxide is 0.5 to 35.0 wt % and more preferably 2.0 to 25 wt % based on the total weight of the cosmetic.

It is an objective of performing surface treatment according to the present invention to seal(block) surface active points (sites) of fine particles of titanium oxide and fine particles of zinc oxide to prevent changes in odor or degeneration of the oil agent in the cosmetics or discoloration or color fading of statutory tar pigments (organic pigments). It is a further objective to assimilate surface properties of fine particles of titanium oxide and fine particles of zinc oxide for improving dispersibility thereof into cosmetics.

Meritorious effects of the invention are summarized as follows.

The cosmetics of the present invention exhibit high ultraviolet ray shielding effect, good dispersibility, suppressed photochemical reactivity and catalytic activity and superior stability with lapse of time.

By surface-treating with the silicone oil agent for sealing the surface active points of the fine particles of titanium oxide and fine particles of zinc oxide and by incorporating a composition of these two types of fine particles with a ratio of 9.8:0.2 to 5:5 into cosmetics, the resulting cosmetics are superior in sustained ultraviolet ray shielding effects and in stability by the synergistic effects.

DESCRIPTION OF THE PREFERRED EMBODIMENTS

The surface treatment agent employed in the present invention includes silicone oils, such as dimethyl polysiloxane, methyl hydrogen polysiloxane or alkyl polysiloxane etc.

As the surface treatment agents, used for surface treatment by a jetting method as disclosed in JP Patent Kokoku Publication (JP-B-6-59397 (1994), silicone oils not having reactive groups such as dimethyl polysiloxane, methyl phenyl polysiloxane, perfluoro silicone or polyether modified silicone etc., may be employed. However, it is more preferred to use silicone oils having reactive groups such as methyl hydrogen polysiloxane, trimethylsiloxy silicate etc., or alkyl polysiloxane having functional groups in one terminal or in a side chain of a silicone molecule.

The above-mentioned alkyl polysiloxane may be enumerated by dimethyl polysiloxy silazane, α-monohydroxy siloxane, α, ω-dihydroxy polydimethyl siloxane, α-monoalkoxy polydimethyl siloxane, α-dialkoxy polydimethyl siloxane, α-trialkoxy polydimethyl siloxane (e.g., α-triethoxy polydimethyl siloxane etc.), α, ω-dialkoxy polydimethyl siloxane, α, ω-hexaalkoxy polydimethyl siloxane dimethyl polysiloxy chloride, dimethyl polysiloxy bromide and dimethyl polysiloxy iodine and the like.

The surface treatment method is the method practiced customarily, such as a mechano-chemical method, a solvent method or a jet method as disclosed in JP-Patent Kokoku Publication JP-B-6-59397 (1994). The coating amount of the surface treatment agent is 1 to 20 wt %. The surface-treated silicone, treated by these methods, is chemically bonded with the surface of the surface-activated ultraviolet ray shielding material. The state of coating is presumed to be a resinous or gelated coating on the active point (site) of the ultraviolet ray shielding material.

Among the above methods for surface treatment, the jet method, disclosed in JP-Patent Kokoku Publication JP-B-6-59397 (1994), is most preferred. This jet method resides in applying an impact force by an ejected air stream to a mixture of powder particles and the surface treatment agent (silicone oil agent) for mechano-chemically surface-treating the pulverulent material for causing the surface treatment agent to be adsorbed or bonded to the powder surface to produce surface-treated powders. It is possible with this method to produce a surface-treated powder having uniform properties of the powdered particles and improved surface properties.

Namely, the jet method is such a method in which a pressured gas, such as pressurized air or steam, is ejected at a high speed via a nozzle to generate a jet stream into which the powder particles and the surface treatment agent are entrained for pulverizing or de-agglomerating the powder particles by collision and/or attrition of the powder particles with one another, and in which the surface treatment agent is adsorbed or bonded to the pulverized or de-agglomerated particles.

With the jet method, the powders and the surface treatment agent are collided against one another at a high speed of tens to hundreds of meters per second so that the powders are further pulverized or de-agglomerated under the energy of collision, at the same time as the surface treatment agent having high surface activity undergoes uniform and strong (chemical) adsorption or bonding. The surface treatment agent is adsorbed or bonded to surface active points (sites) of the fine particles of titanium oxide and the fine particles of zinc oxide to seal the surface active points. The surface treatment agent is uniformly adsorbed or bonded to the surface of the treated powders before contamination with other substances or before occurrence of secondary flocculation. The particles of the powders prior to treatment by the jet method may be primary particles, secondary particles or a mixture thereof.

With the jet method, the surface treatment agent may be affixed to the surface of each of the fine particles resulting from pulverization or de-agglomeration without flocculation of the fine particles. In this manner, surface treated powders free from secondary flocculation may be produced by the jet method, while particles of secondary flocculation may also be produced by changing the conditions, such as by partially changing component parts of the producing equipment.

The surface treatment by the jet method may be performed by employing a jet gas stream type pulverizer. Specifically, a mixture of the powder particles and the surface treatment agent is charged into a jet gas stream type pulverizer and the impact force by the ejected gas stream is applied to the mixture. The mixture is agitated in a fluidized state in the pulverizer for mechano-chemically surface-treating the powders thereby adsorbing or bonding the surface treatment agent to the powder surface.

The jet gas stream type pulverizer may be of a fluidized bed type, a spiral type or jet atomizer (jet-o-mizer) type. The fluidized bed type is most preferred since it assures uniform and efficient treatment.

The mean particle size of fine particles of zinc oxide, surface-treated with dimethyl polysiloxane or hydrogen polysiloxane of the composition of the present invention, that is secondary flocculated particles, as measured by the laser diffraction method, is 0.2 to 3.5 μm. The secondary flocculated particles mean a collection state of particles in which particles in a state approximate to that of the primary particles are flocculated with a weak force by silicone processing.

The mean particle size of the secondary flocculated particles of fine particles of zinc oxide prior to surface treatment is 5 to 12 μm, as measured by the laser diffraction method. Such particle size may be reduced by the surface treatment to 0.5 to 2.7 μm, so that, if the particles, thus surface treated, are contained in the cosmetics, the resulting cosmetics may be improved in dispersibility, adhesion and durability of the ultraviolet shielding effects. In addition, the surface-treated fine particles of zinc oxide are inorganic and high in safety with respect to the skin, while providing the convergence, anti-inflammatory effects and in anti-bacterial performance, as well.

Through division into ultra-fine (or superfine) particles, zinc oxide is increased in surface activity and in flocculation between particles, while being occasionally aggregated or agglomerated. Judging from the degree of discoloration of statutory dyes (organic colors), the surface activity of the ultra-fine particles of zinc oxide presumably is about five times as high as that of ultra-fine particles of titanium oxide. In addition, the ultra-fine particles of zinc oxide exhibit strong catalytic activity and are liable to cause changes in odor or decomposition of the cosmetic oil agent. In order to overcome these defects, the fine particles of zinc oxide may be surface-treated with silicone oil to give secondary flocculated particles which are close to the primary particles and which seal the surface active points of the fine particles of zinc oxide. By incorporating the surface-processed fine particles of zinc oxide into the cosmetics, the resulting cosmetics may be improved in stability.

Any known method for producing ultra-fine particles of zinc oxide according to the present invention may be employed provided that the method employed gives ultra-fine to fine particles of zinc oxide. For example, the fine particles of zinc oxide, produced by methods disclosed in JP Patent Kokai Publications Nos. JA-A-57-20319 (1982), 3-199121 (1991), 4-280184 (1992), or JA-B-2-196029 (1990) may be employed.

The particle size of the primary particles of the fine particles of zinc oxide, employed in the present invention, is preferably 0.01 to 0.1 μm, more preferably 0.03 to 0.1 μm and most preferably 0.03 to 0.06 μm.

The surface-treated fine particles of zinc oxide, having the above characteristics, have the properties of blocking the UV-A range. However, these particles are of a titer value such that the SPF value is increased by about 1 for 1 wt % of the fine particles. If high SPF values are desired with the fine particles of zinc oxide alone, it is necessary to use a high ratio of the fine particles. For example, if a lotion with a viscosity of 8,000 to 12,000 is desired, much viscous creamier product may occasionally result, namely, a desired dosage form cannot be achieved.

The mean particle size of fine particles (secondary flocculated particles) of titanium oxide, surface-treated with dimethyl polysiloxane or hydrogen polysiloxane of the composition of the present invention, is 0.5 to 3.0 μm, as measured with the laser diffraction method.

The mean particle size of non-treated flocculated ultra-fine particles of titanium oxide is 1.2 to 5.0 μm, as measured by the laser diffraction method. Since strong active points remain, irradiation with ultraviolet light of the ultra-fine particles decomposes adsorbed water to generate OH and $OH_2$ free radicals having a strong force of oxidation. These free radicals cause discoloration or fading of the statutory tar dyes for cosmetics or degeneration of the oil agents for general cosmetics. On the other hand, as for the ultraviolet light protection effect, the ultra-fine particles of titanium oxide have a titer value which is three to four times as high as that of the fine particles of zinc oxide and hence are effective in producing high SPF values. However if the ultra-fine particles of titanium oxide are incorporated in the cosmetics, it presents a pale white color on skin and aesthetically unsatisfactory. Thus there is still a problem to be solved in order to attain a higher SPF value without such deficiencies. On the other hand, the ultra-fine particles of titanium oxide exhibit strong surface activity and hence tend to undergo re-flocculation with lapse of time to lower the SPF value.

The ultra-fine particles of titanium oxide, having a limited primary particle size of 10 to 50 nm, exhibit the strongest biological effects and exhibit such characteristics that they reflect and scatter ultraviolet rays of 290 to 320 nm liable to produce erythema and inflammatory diseases on the skin while allowing for good transmission of visible light. However, the commercially available ultra-fine particles undergo strong flocculation among particles due to strong surface activity and a minor amount of adsorbed moisture. Thus the particle size exhibiting optical properties of light scattering is centered about the scattering ranging from the Raleigh area to the Mie area, such that transparency is substantially lowered. Therefore, in the cosmetics containing these ultra-fine particles, the applied film of the cosmetics become outstanding in pale white color or the particles scattered by the mechanical force tend to be re-flocculated with lapse of time due to strong surface activity. Thus the SPF value is lowered to render it difficult to produce the desired ultraviolet light protective effect.

Any known method for producing ultra-fine particles of titanium oxide according to the present invention may be employed provided that the method employed gives ultra-fine to fine particles of titanium oxide. For example, the fine particles of titanium oxide, produced by methods disclosed in JP Patent Kokai Publication Nos.2-194065 (1990), 2-196028 (1990) or 2-196029 (1990) may be employed, too.

The particle size of the primary particles of the fine particles of titanium oxide, employed in the present invention, is preferably 0.01 to 0.1 μm, more preferably 0.03 to 0.1 μm and most preferably 0.03 to 0.06 μm.

By surface-treating these ultra-fine and fine particles of titanium oxide with dimethyl polysiloxane or hydrogen polysiloxane for sealing surface active points thereof, it becomes possible to prevent degeneration or change in odor of the oil agents for general cosmetics, discoloration or fading of statutory tar dyes (organic colors) for cosmetics or re-flocculation of particles with lapse of time and to achieve a small mean particle size and prolonged durable ultraviolet protection effects as well as to improve dispersibility and adhesion to the skin.

The composition of the inventive cosmetics contains fine particles of titanium oxide and fine particles of zinc oxide, surface-treated with dimethyl polysiloxane or hydrogen polysiloxane, with the ratio being 9.8:0.2 to 5:5, preferably 9:1 to 6:4 and more preferably 8:2 to 6.8:3.2. If the fine particles of titanium oxide and zinc oxide, surface-processed by the jet method as disclosed in the above referenced JP Patent Kokoku publication JP-B-6-59397 (1994), are contained in the composition, the two kinds of the fine particles may be mixed in the same ratios as mentioned above. It has been found that the composition in the above range of proportions has an SPF value higher than that of the surface-treated fine particles of titanium oxide alone, having high ultraviolet shielding effects, and that the composition has sustained effect and superior stability with lapse of time and is suppressed in photochemical reactivity or catalytic activity.

The operating mechanism is scrutinized, e.g., in the case of an emulsified product, the surface-treated fine particles of titanium oxide and fine particles of zinc oxide, dispersed in oil particles, are in the dispersed state, since these are insufficient in compatibility with the oil agents for cosmetics in general and hence a repulsive force operates to some extent between the fine particles of titanium oxide and zinc oxide and the oil agent in the oil particles. On the other hand, the layers of the surface treating agent sealing the surface active points exhibit barrier effects prohibiting the surface-treated fine particles of titanium oxide and zinc oxide from approaching towards each other thus allowing the dispersed state of those particles to be maintained.

The reason the SPF value is increased in the emulsified product and powdered product by employing both the fine particles of titanium oxide surface-modified with silicone and fine particles of zinc oxide surface-modified with silicone is presumably that, by the processing by the jet method, the dispersed silicone-treated fine particles of zinc oxide are intruded around the dispersed, silicone-treated fine particles of titanium oxide, with the silicone-treated fine particles of zinc oxide operating as a spacer for improving dispersibility of the silicone-treated fine particles of titanium oxide and suppressing re-flocculation of the silicone-treated fine particles of titanium oxide. That is, the SPF value is presumably improved since the silicone-treated fine particles of zinc oxide which is intruding between the silicone-treated fine particles of titanium oxide operate as one component with the silicone-treated fine particles of titanium oxide.

For higher SPF value, it is effective to use the silicone-treated fine particles of titanium oxide in larger quantities than the silicone-treated fine particles of zinc oxide. The reason for such combination to exhibit higher SPF value with specific ratio is presumably that the silicone-treated fine particles of titanium oxide or the silicone-treated fine particles of zinc oxide are present in an excess amount exceeding the range of amounts required for operating as a spacer, thus the silicone-treated fine particles of titanium oxide are re-flocculated with one another or the silicone-treated fine particles of zinc oxide are re-flocculated with one another, thus lowering the SPF value. The spacer effect is presumably determined by the difference in specific gravity, volume ratio or the particle size of the two kinds of the fine particles employed.

The reason the maximum SPF ratio is displayed for the amount of the surface-treated fine particles of titanium oxide being larger than that of the surface-treated fine particles of titanium oxide presumably resides in a specific mechanism of multiple scattering. That is, if the cosmetic comprises only the surface-treated fine particles of titanium oxide, the incident light is scattered by the oil agent in the liquid drop and by the particle surface, whereas, if the surface-treated fine particles of zinc oxide (refractive index, 2.0) are intruded around the surface-treated fine particles of titanium oxide (refractive index, 2.65), the incident light undergoes scattering in a space between the oil agent in the oil drops and the surface-treated fine particles of titanium oxide, with the transmitted light being further scattered on the surface of the surface-treated fine particles of zinc oxide. On the other hand, with the cosmetics comprising only the surface-treated zinc oxide, surface-treated fine particles of zinc oxide are lower in the refractive index than the surface-treated fine particles of titanium oxide, such cosmetics are weaker in light scattering and increased in light transmittance, so that the SPF value is low. In addition, in a composition in which the surface-treated fine particles of zinc oxide is higher (in ratio) than the surface-treated fine particles of titanium oxide, the multiple scattering between the oil agent of the oil drops and the surface treated fine particles of zinc oxide and fine particles of titanium oxide occurs consistently, however, the light transmittance is increased proportionate to the amount of the surface-treated fine particles of zinc oxide having the low refractive index exceeding that of the surface-treated fine particles of titanium oxide, thus lowering the SPF value.

The amount of the composition composed of the surface-treated fine particles of titanium oxide and the surface-treated fine particles of zinc oxide is 0.5 to 12.5 wt % and preferably 1.0 to 10 wt % based on the total quantity of the cosmetics, respectively. If the amount of the composition is smaller than 1.0 wt.%, it is not possible to prevent skin drying or lowering of the skin function such as inflammation or skin pigmentation. If the amount of the composition exceeds 12.5 wt %, the ultraviolet ray shielding effect is not increased in proportion to the increased amount, which is an economic disadvantage. In addition, such cosmetics are low in extendibility and adhesion thus lacking in durability of the ultraviolet ray shielding effect. There is also the limitation on the dosage, since the lotion type cosmetics (with the viscosity ranging between 8000 and 12000 cps) are difficult to manufacture with such higher loading of the pigments.

If the total weight of the composition composed of the silicone-treated fine particles of titanium oxide and the silicone-treated fine particles of zinc oxide, obtained on surface treatment by the jet method of the JP Patent Kokoku Publication JP-B-6-59397 (1994), is 0.5 to 35.0 wt % based on the total weight of the cosmetics, the above problem is not raised. However, the above ratio is preferably 0.5 to 25.0 wt %, more preferably 1.0 to 25.0 wt %, most preferably 2.0 to 25.0 wt % and by far the most preferably 2.0 to 12.5 wt %.

The cosmetics of the present invention may be used for any types of the lotion, milky lotion, cream, oil foundation or emulsified foundation. Although there is no definition, a part with a wider usable area is preferably considered.

EXAMPLES

The present invention will now be explained with reference to illustrative Examples which are not intended for limiting the invention. In the following Examples, the parts denote parts by weight. As the method for processing the surface of titanium oxide and zinc oxide with the silicone oil agent, the jet method as shown in JP Patent Kokoku publication JP-B-6-59397 (1994) was used.

Example 1
Lotion

| | |
|---|---|
| squalane | 14 |
| jojoba oil | 4 |
| olive oil | 2 |
| cetanol | 0.5 |
| vaseline | 1 |
| bees wax | 0.6 |
| sorbitan monostearate | 2.1 |
| polyoxyethylene behenyl ether | 2.3 |
| butylparaben | 0.1 |
| fine particles of zinc oxide processed with 5% dimethyl polysiloxane (mean particle size, 1.6 μm) | 2.0 |
| fine particles of titanium oxide processed with 5% dimethyl polysiloxane (mean particle size, 1.2 μm) | 8.0 |
| 1,3 butylene glycol | 5.0 |
| glycerine | 2.0 |
| xanthane rubber | 0.01 |
| carboxymethyl cellulose sodium salt | 0.14 |
| perfume | 0.1 |
| purified water | 56.15 |

Example 2
Cream

| | |
|---|---|
| behenic acid | 1.0 |
| cetanol | 0.5 |
| cholesterol | 1.0 |
| olive oil | 1.0 |
| bees wax | 2.0 |
| octyldodecyl myristate | 5.0 |
| squalane | 11.0 |
| vaseline | 1.0 |
| sorbitan monostearate | 1.6 |
| butylparaben | 0.1 |
| purified lanoline | 3.5 |
| polyethylene glycol monostearate | 1.8 |
| fine particles of zinc oxide processed with 20% dimethyl polysiloxane (mean particle size, 2.69 μm) | 0.2 |
| fine particles of zinc oxide processed with 1% methyl hydrogen polysiloxane (mean particle size, 0.70 μm) | 9.8 |
| propylene glycol | 2.0 |
| 1,3 butylene glycol | 3.0 |
| triethanolamine | 0.3 |
| methylparaben | 0.2 |
| purified water | 55.0 |

Example 3
Beauty Wash

| | |
|---|---|
| purified water | 88.9 |
| propylene glycol | 1.0 |
| polyoxyethylene hardened castor oil | 0.4 |
| ethanol | 8.0 |
| fine particles of titanium oxide processed with 20% dimethyl polysiloxane (mean particle size, 1.5 μm) | 0.68 |
| fine particles of zinc oxide processed with 1% methyl hydrogen polysiloxane (mean particle size, 0.71 μm) | 0.32 |
| allantoin | 0.05 |
| citric acid | 0.02 |
| sodium hydrogen phosphate | 0.13 |
| sorbitol | 0.2 |
| L-cerin | 0.2 |
| EDTA2NA | 0.1 |

Example 4
Oily Foundation

| | |
|---|---|
| squalane | 56.8 |
| cetyl octanoate | 5.0 |
| micro-crystalline wax | 6.0 |
| talc | 10.0 |
| fine particles of zinc oxide processed with 1% dimethyl polysiloxane (mean particle size, 0.5 μm) | 5.1 |
| fine particles of titanium oxide processed with 20% dimethyl polysiloxane (mean particle size, 1.7 μmm) | 4.9 |
| colored pigment | 12.0 |
| perfume | 0.2 |

Example 5
Emulsified Type Foundation

| | |
|---|---|
| stearic acid | 1.75 |
| cetyl octanoate | 3.0 |
| polyethylene glycol monostearate | 2.0 |
| glycerin monostearate | 3.0 |
| pigment paste | 15.0 |
| fine particles of zinc oxide processed with 20% dimethyl polysiloxane (mean particle size, 2.3 μm) | 3.0 |
| fine particles of titanium oxide processed with 1% methyl hydrogen polysiloxane (mean particle size, 0.7 μm) | 7.0 |

-continued

| | |
|---|---|
| butylparaben | 0.1 |
| P.E.G (polyethylene glycol) | 6.0 |
| carboxy methyl cellulose sodium salt | 0.1 |
| methylparaben | 0.2 |
| triethanolamine | 0.7 |
| magnesium aluminum silicate | 1.0 |
| purified water | 57.15 |

Example 6

| | |
|---|---|
| powder foundation | 61.3 |
| fluorinated sericite | 8.0 |
| recitinated titanium oxide | 15.0 |
| nylon powder | 2.4 |
| fine particles of zinc oxide processed with 20% methyl hydrogen polysiloxane (mean particle size, 2.7 μm) | 2.4 |
| fine particles of titanium oxide processed with 5% dimethyl polysiloxane (mean particle size, 2.7 μm) | 9.6 |
| iron oxide red | 1.0 |
| iron oxide hydride | 2.1 |
| ultramarine | 0.4 |
| perfume | 0.2 |

Example 7
Powder Foundation

| | |
|---|---|
| talc | 7.5 |
| sericite | 20.0 |
| mica powders | 12.5 |
| titanium oxide | 7.0 |
| fine particles of titanium oxide processed with 5% dimethyl polysiloxane (mean particle size, 0.9 μm) | 10.0 |
| fine particles of zinc oxide processed with 5% dimethyl polysiloxane (mean particle size, 1.8 μm) | 25.0 |
| yellow iron oxide | 3.5 |
| black iron oxide | 0.5 |
| iron oxide red | 2.0 |
| liquid paraffin | 5.0 |
| stearyl alcohol | 3.0 |
| bees wax | 3.0 |
| squalane | 1.0 |

Several production examples of silicone-treated fine particles of titanium oxide and silicone-treated fine particles of zinc oxide are given below.

Production Example (1)

10 kgs of a mixture of titanium oxide (manufactured by ISHIHARA SANGYO KK under the trade name of TTO-55A) and zinc oxide (manufactured by SUMITOMO OSAKA CEMENT under the trade name of ZnO-31), with a weight mixing ratio of 8:2, were mixed together with 500 gs of dimethyl polysiloxy silazane by a Henschel mixer and pulverized by a fluidized bed type jet mill manufactured by ALPINE INC. under the trade name of 100 AFG under a nozzle air pressure of 5 kg/cm² to produce a composition composed of fine particles of titanium oxide surface-modified with 5% dimethyl polysiloxane and fine particles of zinc oxide surface-modified with 5% dimethyl polysiloxane with a weight ratio of 8:2.

Production Example (2)

5 kgs of titanium oxide (manufactured by TEIKOKU KAKO KK. under the trade name of TTO-55A) and 50 gs of methyl hydrogen polysiloxane were mixed together by a Henschel mixer and pulverized by the above jet mill under an air pressure of 6 kg/cm² to produce fine particles of titanium oxide surface-modified with 1% methyl hydrogen polysiloxane. 3 kgs of zinc oxide (manufactured by SAKAI KAGAKU KK. under the trade name of FINEX-50) were mixed with 600 gs of polymethyl polymethoxysilane by a Henschel mixer to produce fine particles of zinc oxide surface-modified with 20% dimethyl polysiloxane.

Using the recipe of Examples 1 and 2, the possible presence of surface processing and changes in composition of fine particles of titanium oxide and fine particles of zinc oxide were compared with the composition of JP-Patent Kokai publication JP-A-3-279323 (1991) in terms of the SPF values. The results are shown in Table 1.

For the composition of JP-Patent Kokai publication JP-A-3-279323 (1991), the composition given in paragraph [0041] of the above Patent Publication was used.

Then, changes in SPF after lapse of one year were measured. The results are shown in Table 2.

(1) Photocatalyst Activity Test
(Photochemical Reactivity Test)

A 1:1 composition of fine particles of titanium oxide surface-modified with 5% dimethyl polysiloxane and fine particles of zinc oxide surface-modified in the same way was scrutinized with respect to dyes Y-401 and R-202.

To 18 gs of samples were added 2 gs each of yellow Y-401 and red R-202 and resulting mixtures were further mixed for 15 minutes by a mortar machine. The resulting mixture was irradiated with UV light by a UV lamp at 560 μm/cm² for 20 days. The results are shown in Table 3.

The non-processed samples, mixed with Y-401 and R-202, suffered from significant fading of the pigments, while the samples obtained on surface processing of fine particles of titanium oxide and fine particles of zinc oxide with silicone suffered from color fading to a significantly lesser extent.

(2) Thermal Catalytic Activity Test 10 gs of oil agents, that is 50 cs of silicone manufactured by SHIN-ETSU KAGAKU KOGYO KK under the trade name of KF96, squalane and octyldodecyl oleate) and 0.1 g of each sample were charged into a small glass vial of 20 cc and dispersed for 15 minutes by ultrasonic waves. The dispersed samples were allowed to stand in constant temperature driers of 90° C. and 150° C., respectively. The test was stopped at a time point when any of the samples underwent discoloration or color fading. The degree of oxidation and changes in structure of the oil agents at such time were checked using a Fourier transformation infrared spectrometer (FT-IR). The results are shown in Table 4.

As compared to non-processed compositions and blanks, the surface-treated compositions were low in P.O.V value (peroxide value) such that the oil agents were maintained in the stabled state.

The fine particles of oxides put to the accelerated tests were checked as to color changes. It was found that surface-treated samples maintained white appearance, while non-processed samples presented brownish color. The results are shown in Table 5.

The results of the accelerated test (at 150° C., two hours) indicated that surface treated samples had substantially the same value as the blanks and underwent no changes in structure, while the non-processed samples showed a low peak height ratio thus indicated changes in structure.

As may be seen from the above results, the cosmetics of the present invention exhibit superior dispersibility, high ultraviolet ray shielding effects, suppressed photochemical reactivity and catalytic activity and excellent stability with lapse of time.

Meanwhile, the sun protective factor (SPF) value was measured by the following sequence using an SPF analyzer manufactured by Optometric Inc. under the trade name of SPF-290 Analyzer.

Sequence 1 (For Powder Foundation)

(i) On a quartz plate of 100 mm in length, 100 mm in width and 3 mm in height was applied a transpore surgical tape manufactured by 3M Inc. On this tape was secured a sample coating area which is 6.4 cm by 6.4 cm (40 cm²).

(ii) On the area for sample coating was applied 0.05 g of a sample (1.25 mg/cm²) using a sponge puff.

(iii) Using the SPF analyzer, a measurement light beam of 16 mmø in diameter was radiated on the coating area. Measurement was carried out for nine spots and a mean value of the nine measured values was used as an SPF value.

(iv) Depending on samples, the above sequence of operations was repeated several times to get a mean value.

Sequence 2 (For Liquid Foundation or Cream)

(i) On a quartz plate of 100 mm in length, 100 mm in width and 3 mm in height was applied a transpore surgical tape manufactured by 3M Inc. On this tape was secured a sample coating area which is 6.4 cm by 6.4 cm (40 cm²).

(ii) On the area for sample coating was applied 0.08 g of a sample (2.0 mg/cm²) using a sponge puff. The sample was then allowed to stand for 15 minutes.

(iii) Using the SPF analyzer, a measurement light beam of 16 mmø in diameter was radiated on the coating area. Measurement was carried out for nine spots and a mean value of the nine measured values was used as an SPF value.

(iv) Depending on samples, the above sequence of operations was repeated several times to get a mean value.

It is shown below that the jet method disclosed in JP Patent Kokoku Publication JP-B-6-59397 (1994) is preferred as the method for surface-modifying fine particles of titanium oxide and fine particles of zinc oxide.

The silicone-treated fine particles of titanium oxide and the silicone-treated fine particles of zinc oxide, produced by the method described in JP-Patent Kokai Publication JP-A-62-228006 (1987) and the silicone-treated fine particles of titanium oxide and the silicone-treated fine particles of zinc oxide, produced by the jet method described in JP-Patent Kokoku Publication JP-B-6-59397 (1994) were evaluated as to dispersibility, SPF value and hydrophobicity.

The method described in JP Patent Kokai Publication JP-A-62-228006 (1987) consists in thoroughly mixing titanium oxide or zinc oxide with the silicone oil dissolved in a solvent under heating by a low-speed blender, distilling off the solvent and heating the resulting mass at 90° to 450° C.

As the silicone-treated fine particles of titanium oxide and the silicone-treated fine particles of zinc oxide, produced by the jet method described in JP-Patent Kokoku Publication JP-B-6-59397 (1994), those produced by the same method as that described in the production example (2) were used.

Items and Method of Evaluation (Dispersibility)

5 gs of the fine particles of titanium oxide and fine particles of zinc oxide (1:1), processed as described above, were accurately weighed out on liquid paraffin and the resulting mass was agitated for five minutes at an r.p.m. of 300 to give a paste. Using a particle gauge (Hegmen gauge; range of particles, from 0 to 25 μm), the particle diameter where there exists the flocculated mass was measured three times.

(SPF Value)

The paste used for evaluating the dispersibility was measured five times by the In-Vitro method, using an SPF analyzer manufactured by Optometrics Inc. under the trade name of SPF-290 Analyzer, in accordance with the sequence (2) above.

(Hydrophobicity)

10 ml of purified water was weighed out in a 20 ml test tube and 0.1 g of silicone-treated powders was weighed out accurately in (1) and (2). These weighed out amounts were stirred strongly with hand 100 times and allowed to stand at room temperature for one day. The resulting mass was further stirred 100 times and, on the next day, the status of the silicone-treated powders collected at the water-air boundary was evaluated.

Excellent (⊚): the silicone-treated powders are collected completely at the water-air interface, with water as the dispersion medium being fully transparent.

Good (○): most of the silicone-treated powders are collected at the water-air interface, however, the water as the dispersion medium becomes semi-transparent, with particles being partially dispersed and partially precipitated on the test tube bottom.

With the method described in JP-Patent Kokai publication JP-A-62-228006 (1987), the dispersibility, SPF value and the hydrophobicity were 20 μm, 14.8 and ○, respectively. With the above jet method, the dispersibility, SPF value and the hydrophobicity were 5 μm, 21.2 and ⊚, respectively.

As may be seen from the above results, the size of the particle mass obtained with the jet method is about one quarter that with the method disclosed in the Publication. As to the SPF value and hydrophobicity, the jet method is evidently superior.

It should be noted that any modification may be done without departing the gist and scope of the present invention as disclosed herein and claimed in the appended claims.

TABLE 1

| Recipe | Surface Processed or not | Titanium Oxide to Zinc Oxide Ratio for 10 wt. % Addition in Cosmetics | | | | | | | | |
|---|---|---|---|---|---|---|---|---|---|---|
| | | TiO₂10% | 9.8:0.2 | 9:1 | 8:2 | 7:3 | 6:4 | 5:5 | 3:7 | ZnO10% |
| Ex.1 | Processed | 32.6 | 36.0 | 41.1 | 44.1 | 43.5 | 40.0 | 34.6 | 21.3 | 10.8 |
| | not | 27.5 | 27.7 | 28.6 | 29.0 | 30.0 | 27.5 | 21.4 | 11.8 | 7.9 |
| Ex.2 | Processed | 31.9 | 35.1 | 40.5 | 43.6 | 42.8 | 39.4 | 33.9 | 20.8 | 10.1 |
| | not | 26.8 | 26.8 | 27.9 | 28.9 | 27.0 | 26.2 | 20.8 | 11.3 | 7.5 |
| JP-A-3-279323 | — | 31.9 | 32.0 | 32.5 | 34.6 | 35.3 | 30.1 | 25.0 | 15.3 | 9.9 |

The coating amount was 1.2 mg/cm².

TABLE 2

| Recipe | Surface Processed or not | Titanium Oxide to Zinc Oxide Ratio for 10 wt. % Addition in Cosmetics | | | | | | | | |
|---|---|---|---|---|---|---|---|---|---|---|
| | | 10:0 | 9.8:02 | 9:1 | 8:2 | 7:3 | 6:4 | 5:5 | 3:7 | 0:10 |
| Ex.1 | Processed | 32.6 | 36.0 | 41.1 | 44.1 | 43.5 | 40.0 | 34.6 | 21.5 | 10.8 |
| | Processed | 32.5 | 36.1 | 41.1 | 44.2 | 43.5 | 40.0 | 35.0 | 20.9 | 10:8 |
| | not | 27.5 | 27.7 | 28.6 | 29.0 | 30.0 | 27.5 | 21.4 | 11.8 | 7.9 |
| | not | 20.5 | 20.7 | 21.8 | 21.5 | 23.0 | 20.5 | 16.8 | 4.9 | 1.8 |
| JP-A-3-279232 | — | 31.9 | 32.0 | 32.5 | 34.6 | 35.3 | 30.1 | 25.0 | 15.3 | 9.9 |
| | | 25.1 | 25.0 | 25.5 | 27.4 | 27.9 | 22.5 | 18.0 | 8.3 | 2.9 |

Upper and Lower rows stand for SPF Values when left at room temperature for one year.

TABLE 3

| Pigment | Surface Processed or not | | Colormetric Value (L. ab) | | |
|---|---|---|---|---|---|
| Y-401 | Not Processed | Before Irradiation | 65.60 | 0.69 | 65.92 |
| | | After Irradiation | 52.87 | 1.88 | 44.13 |
| | Fine Particles of Titamium Oxide Processed similarly to Fine Particles of Titanium Oxide Processed with 5% Dimethyl Polysiloxane (1:1) | Before Irradiation | 66.74 | 1.36 | 67.81 |
| | | After Irradiation | 67.63 | 1.01 | 67.11 |
| R-202 | Not Processed | Before Irradiation | 37.54 | 36.14 | 19.66 |
| | | After Irradiation | 42.12 | 29.64 | 5.31 |
| | Fine Particles of Zinc Oxide Processed similarly to Fine Particles of Titanium Oxide Processed with 5% Dimethyl Polysiloxane (1:1) | Before Irradiation | 35.22 | 33.21 | 19.36 |
| | | After Irradiation | 36.23 | 34.09 | 18.91 |

TABLE 4

Results of Measurement of POV Values

| Type of Surface | Type of Oil Agent | 90° C./5 h | 150° C./2 h |
|---|---|---|---|
| Not Processed | Squalane | 0.1 or less | 16.8 |
| | Octyldodecyl Oleinate | 8.9 | 11.0 |
| Composition of Dimethyl Polysiloxane Processed ZnO and TiO$_2$ (1:1) | Squalane | 0.1 or less | 5.5 |
| Blank | Octyldodecyl Oleinate | 8.8 | 9.9 |
| | Squalene | 0.1 or less | 12.0 |
| | Octyldodecyl Oleinate | 9.0 | 10.1 |

TABLE 5

Peak Height Ratio of Absorbance by Atomic Group by FT-IR

| State of Oil Agent | 90° C./5 h | 150° C./2 h |
|---|---|---|

1. For KF96 (50 cs), peak height ratio of 1256 cm$^{-1}$ (Si—CH$_2$)/2962 cm$^{-1}$ (—CH$_2$) was used.

| | | |
|---|---|---|
| Blank | 2.564 | 2.593 |
| Not Processed | 2.518 | 1.889 |
| Fine Particles of Titanium Oxide and Fine Particles of Zinc Oxide Processed with 5% Dimethyl Polysiloxane | 2.579 | 2.629 |

TABLE 5-continued

Peak Height Ratio of Absorbance by Atomic Group by FT-IR

| State of Oil Agent | 90° C./5 h | 150° C./2 h |
|---|---|---|

2. For squalane, peak height ratio of 2954 cm$^{-1}$ (—CH$^3$)/1464 cm$^{-1}$ (=CH2) was used.

| | | |
|---|---|---|
| Blank | 3.067 | 3.060 |
| Not Processed | 3.175 | 2.452 |
| Fine Particles of Titanium Oxide and Fine Particles of Zinc Oxide Processed with 5% Dimethyl Polysiloxane | 3.087 | 2.970 |

3. For octyldodecyl oleinate, peak height ratio of 2954 cm$^{-1}$ (—CH$^2$)/1740 cm$^{-1}$ (=C=O) was used.

| | | |
|---|---|---|
| Blank | 2.295 | 2.263 |
| Not Processed | 2.346 | 1.316 |
| Fine Particles of Titanium Oxide and Fine Particles of Zinc Oxide Processed with 5% Dimethyl Polysiloxane | 2.297 | 2.294 |

What is claimed is:

1. A cosmetic comprising file particles of titanium oxide surface-modified with silicone and fine particles of zinc oxide surface-modified with silicon, wherein the ratio of the fine particles of titanium oxide surface-modified with silicone to the fine particles of zinc oxide surface-modified with silicone is 9.8:0.2 to 5:5. the mean particle size of secondary flocculation of fine particles of titanium oxide is 0.5 to 3.0

μm, and the mean particle size of secondary flocculation of fine particles of zinc oxide is 0.2 to 3.5 μm.

2. The cosmetic as defined in claim 1 wherein the total weight of the fine particles of titanium oxide and the fine particles of zinc oxide is 0.5 to 12.5 wt % based on the total weight of the cosmetic.

3. The cosmetic as defined in claim 1 wherein the total weight of the fine particles of titanium oxide and the fine particles of zinc oxide is 1.0 to 10 wt % based on the total weight of the cosmetic.

4. The cosmetic as defined in claim 1 wherein said silicone is selected from the group consisting of silicone oils having reactive group or groups.

5. The cosmetic as defined in claim 4 wherein said silicone is selected from the group consisting of methyl hydrogen-polysiloxane, trimethylsiloxy silicate, and alkyl polysiloxane having functional groups in one terminal or in a side chain of a silicone molecule.

6. A cosmetic comprising fine particles of titanium oxide surface-modified with silicone and fine particles of zinc oxide surface-modified with silicone, said silicone-treated fine particles of titanium oxide being obtained by pulverizing or de-agglomerating titanium oxide by a jet stream and by simultaneously adsorbing and bonding silicone and said silicone-treated fine particles of zinc oxide being obtained by pulverizing or de-agglomerating titanium oxide by a jet stream or by simultaneously adsorbing and bonding silicone, wherein the ratio of the fine particles of titanium oxide surface-modified with silicone to the fine particles of zinc oxide surface-modified with silicone is 9.8:0.2 to 5:5.

7. The cosmetic as defined in claim 6 wherein the total amount of the silicone-treated fine particles of titanium oxide and the silicone-treated fine particles of zinc oxide is 0.5 to 35.0 wt % based on the total weight of the cosmetic.

8. The cosmetic as defined in claim 6 wherein the total amount of the silicone-treated fine particles of titanium oxide and the silicone-treated fine particles of zinc oxide is 2.0 to 25.0 wt % based on the total weight of the cosmetic.

9. The cosmetic as defined in claim 6 wherein the mean particle size of secondary flocculation of fine particles of titanium oxide is 0.5 to 3.0 μm and wherein the mean particle size of secondary flocculation of fine particles of zinc oxide is 0.2 to 3.5 μm.

10. The cosmetic as defined in claim 6 wherein said silicone is selected from the group consisting of silicone oils having reactive group or groups.

11. The cosmetic as defined in claim 10 wherein said silicone is selected from the group consisting of methyl hydrogen polysiloxane, trimethylsiloxy silicate, and alkyl polysiloxane having functional groups in one terminal or in a side chain of a silicone molecule.

* * * * *